United States Patent

LeMahieu et al.

[11] 4,281,127
[45] Jul. 28, 1981

[54] TRANS-3-(4-OXO-4H-QUINAZOLIN-3-YL)-2-PROPENOIC ACID DERIVATIVES

[75] Inventors: Ronald A. LeMahieu, North Caldwell; William C. Nason, Mountain Lakes, both of N.J.

[73] Assignee: Hoffmann-La Roche Inc., Nutley, N.J.

[21] Appl. No.: 142,903

[22] Filed: Apr. 23, 1980

Related U.S. Application Data

[63] Continuation-in-part of Ser. No. 55,728, Jul. 9, 1979, abandoned.

[51] Int. Cl.³ .......................................... C07D 239/90
[52] U.S. Cl. .................................. 544/287; 424/251; 544/288
[58] Field of Search ............................... 544/287, 288

[56] References Cited

PUBLICATIONS

Baker et al., J. of Org. Chem., vol. 17, pp. 35–51, (1952).
Yanaiet et al., Yakugaku Zasshi, (J. of Pharm. Soc. of Japan), vol. 86(1), pp. 69–71, (1966).

*Primary Examiner*—Paul M. Coughlan, Jr.
*Attorney, Agent, or Firm*—Jon S. Saxe; Bernard S. Leon; William G. Isgro

[57] ABSTRACT

Trans-3-(4-oxo-4H-quinazolin-3-yl)-2-propenoic acid derivatives of the formula

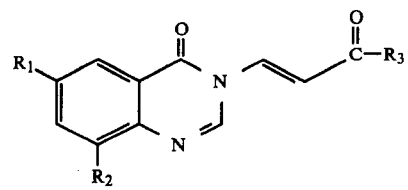

wherein $R_1$ is hydrogen, lower alkyl, lower cycloalkyl, lower alkoxy, hydroxy, halo, lower alkykthio, lower alkylsulfinyl, lower alkylsulfonyl, di-$(C_1-C_7)$alkyl-$N(CH_2)_nO$— or 2-hydroxyethoxy; $R_2$ is hydrogen, lower alkyl or lower alkoxy; $R_3$ is hydroxy, lower alkoxy, di-$(C_1-C_7)$alkyl-$N(CH_2)_nO$— or di-$(C_1-C_7)$alkyl-$N(CH_2)_nNH$—; and n is 2 to 7; provided that at least one of $R_1$ and $R_2$ is other than hydrogen, when $R_3$ is hydroxy, a salt thereof with a pharmaceutically acceptable base, or when $R_3$ is di-$(C_1-C_7)$alkyl-$N(CH_2)_nO$— or di-$(C_1-C_7)$alkyl-$N(CH_2)_nNH$—, a salt thereof with a pharmaceutically acceptable acid, and a process for the preparation thereof, are described. The compounds of formula I are useful as agents in the prevention of allergic reactions.

12 Claims, No Drawings

TRANS-3-(4-OXO-4H-QUINAZOLIN-3-YL)-2-PROPENOIC ACID DERIVATIVES

CROSS-REFERENCE TO RELATED APPLICATIONS

This application is a continuation-in-part of U.S. patent application Ser. No. 55,728, filed July 9, 1979, now abandoned.

BRIEF SUMMARY OF THE INVENTION

The invention relates to trans-3-(4-oxo-4H-quinazolin-3-yl)-2-propenoic acid derivatives of the formula

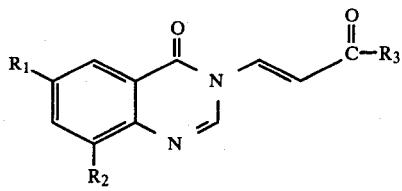

wherein $R_1$ is hydrogen, lower alkyl, lower cycloalkyl, lower alkoxy, hydroxy, halo, lower alkylthio, lower alkylsulfinyl, lower alkylsulfonyl, di-$(C_1$-$C_7)$alkyl-$N(CH_2)_nO$— or 2-hydroxyethoxy; $R_2$ is hydrogen, lower alkyl or lower alkoxy; $R_3$ is hydroxy, lower alkoxy, di-$(C_1$-$C_7)$alkyl-$N(CH_2)_nO$— or di-$(C_1$-$C_7)$alkyl-$N(CH_2)_nNH$—; and n is 2 to 7; provided that at least one of $R_1$ and $R_2$ is other than hydrogen, when $R_3$ is hydroxy, a salt thereof with a pharmaceutically acceptable base, or when $R_3$ is di-$(C_1$-$C_7)$alkyl-$N(CH_2)_nO$— or di-$(C_1$-$C_7)$alkyl-$N(CH_2)_nNH$—, a salt thereof with a pharmaceutically acceptable acid.

As used herein, the term "lower alkyl" denotes a straight or branched chain saturated hydrocarbon containing 1 to 7 carbon atoms, for example, methyl, ethyl, propyl, isopropyl, butyl, t-butyl, neopentyl, pentyl, heptyl, and the like. The term "lower alkoxy" denotes an alkoxy group in which the lower alkyl group is as described above, for example, methoxy, ethoxy, propoxy, pentoxy, and the like. The term "lower alkylthio" denotes an alkylthio group in which the lower alkyl group is as described above, for example, methylthio, ethylthio, propylthio, pentylthio, and the like. The term "lower alkylsulfinyl" denotes an alkylsulfinyl group in which the lower alkyl group is as described above, for example, methylsulfinyl, ethylsulfinyl, and the like. The term "lower alkylsulfonyl" denotes an alkylsulfonyl group in which the lower alkyl group is as described above, for example, methylsulfonyl, ethylsulfonyl, and the like. Exemplary of "lower cyclo($C_3$-$C_7$)alkyl" are cyclopropyl, cyclopentyl, cyclohexyl, and the like. The term "halogen" denotes all the halogens, i.e., bromine, chlorine, fluorine, and iodine. Exemplary of di-$(C_1$-$C_7)$alkyl-$N(CH_2)_nO$— groups are dimethylaminoethoxy, diethylaminoethoxy, dipropylaminoethoxy, diisopropylaminobutoxy, dibutylaminoethoxy, dipentylaminoethoxy, or the like. Exemplary of di-$(C_1$-$C_7)$alkyl-$N(CH_2)_nNH$— groups are dimethylaminoethylamino, diethylaminoethylamino, ethylmethylaminoethylamino, dipropylaminobutylamino, or the like.

DETAILED DESCRIPTION OF THE INVENTION

The invention relates to trans-3-(4-oxo-4H-quinazolin-3-yl)-2-propenoic acid derivatives of the formula

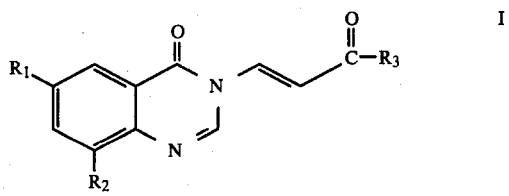

wherein $R_1$ is hydrogen, lower alkyl, lower cyclo($C_3$-$C_7$)alkyl, lower alkoxy, hydroxy, halo, lower alkylthio, lower alkylsulfinyl, lower alkylsulfonyl, di-$(C_1$-$C_7)$alkyl-$N(CH_2)_nO$— or 2-hydroxyethoxy; $R_2$ is hydrogen, lower alkyl or lower alkoxy; and $R_3$ is hydroxy, lower alkoxy, di-$(C_1$-$C_7)$alkyl-$N(CH_2)_nO$— or di-$(C_1$-$C_7)$alkyl-$N(CH_2)_nNH$—; and wherein n is 2 to 7; provided that at least one of $R_1$ and $R_2$ is other than hydrogen, when $R_3$ is hydroxy, a salt thereof with a pharmaceutically acceptable base, or when $R_3$ is di-$(C_1$-$C_7)$alkyl-$N(CH_2)_nO$— or di-$(C_1$-$C_7)$alkyl-$N(CH_2)_nNH$—, a salt thereof with a pharmaceutically acceptable acid.

In a preferred aspect, the invention comprises compounds of formula I wherein $R_2$ is hydrogen, $R_1$ is lower alkyl, lower cyclo($C_3$-$C_7$)alkyl, lower alkoxy, or lower alkylthio, and $R_3$ is as previously described. In another preferred aspect, the invention comprises compounds of formula I, wherein $R_1$ is hydrogen, $R_2$ is lower alkyl or lower alkoxy, and $R_3$ is as previously described. In yet another aspect, the invention comprises compounds of formula I, wherein $R_1$ and $R_2$ are lower alkyl or lower alkoxy, and $R_3$ is as previously described.

Preferred compounds are compounds of formula I wherein $R_1$ is lower alkyl or lower alkylthio, $R_2$ is hydrogen, and $R_3$ is hydroxy or di-$(C_1$-$C_7)$alkyl-$N(CH_2)_nNH$—.

Most preferred compounds of the invention are:
trans-3-(6-Isopropyl-4-oxo-4H-quinazolin-3-yl)-2-propenoic acid;
trans-3-[6-(Methylthio)-4-oxo-4H-quinazolin-3-yl]-2-propenoic acid; and
trans-3-[6-Isopropyl-4-oxo-4H-quinazolin-3-yl]-2-propenoic acid, 2-(diethylamino)ethyl amide hydrochloride.

Other compounds of the invention are described in the Examples and as follows:
trans-3-(6-Ethoxy-4-oxo-4H-quinazolin-3-yl)-2-propenoic acid;
trans-3-(6-n-Propoxy-4-oxo-4H-quinazolin-3-yl)-2-propenoic acid;
trans-3-(6-n-Butoxy-4-oxo-4H-quinazolin-3-yl)-2-propenoic acid;
trans-3-(6-Methyl-4-oxo-4H-quinazolin-3-yl)-2-propenoic acid;
trans-3-(6-Ethyl-4-oxo-4H-quinazolin-3-yl)-2-propenoic acid;
trans-3-(6-n-Propyl-4-oxo-4H-quinazolin-3-yl)-2-propenoic acid;
trans-3-(6-n-Butyl-4-oxo-4H-quinazolin-3-yl)-2-propenoic acid;
trans-3-(6-Bromo-4-oxo-4H-quinazolin-3-yl)-2-propenoic acid;

trans-3-(6-Fluoro-4-oxo-4H-quinazolin-3-yl)-2-propenoic acid;
trans-3-(6-Nitro-4-oxo-4H-quinazolin-3-yl)-2-propenoic acid;
trans-3-(6-Amino-4-oxo-4H-quinazolin-3-yl)-2-propenoic acid;
trans-3-(6-Dimethylamino-4-oxo-4H-quinazolin-3-yl)-2-propenoic acid;
trans-3-(6-Trifluoromethyl-4-oxo-4H-quinazolin-3-yl)-2-propenoic acid;
trans-3-(6-t-butyl-4-oxo-4H-quinazolin-3-yl)-2-propenoic acid;
trans-3-(6-isobutyl-4-oxo-4H-quinazolin-3-yl)-2-propenoic acid;
trans-3-(6-sec-butyl-4-oxo-4H-quinazolin-3-yl)-2-propenoic acid; and the like.

The compounds of the invention can be prepared as illustrated in the following Formula Scheme I:

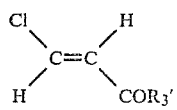

or in the cis configuration, i.e.,

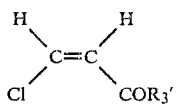

or a mixture thereof, is carried out in the presence of a base such as an alkali metal carbonate such as potassium carbonate, an alkali metal hydride such as sodium hydride, or an alkali metal alkoxide such as sodium methoxide, to yield a compound of formula V. The N-3-alkylation can be carried out at a temperature in the range of from about 25° to about 100° C. using a solvent such as dimethylformamide, acetone or dimethylsulfoxide. When sodium methoxide is the base, a lower alkanol such as methanol can also be used as the solvent. Preferably, the base is potassium carbonate, the solvent is acetone, and the reaction temperature is reflux.

The compounds of formula IV wherein $R'_3$ is alkoxy are known compounds or can be prepared according to known procedures. The compounds of formula IV wherein $R'_3$ is di-$(C_1-C_7)$alkyl-$N(CH_2)_nO$— or di-$(C_1-C_7)$alkyl-$N(CH_2)_nNH$— can be prepared from the known acid chloride of the formula ClCH=CHCOCl which may be in the trans configuration, i.e.,

FORMULA SCHEME I

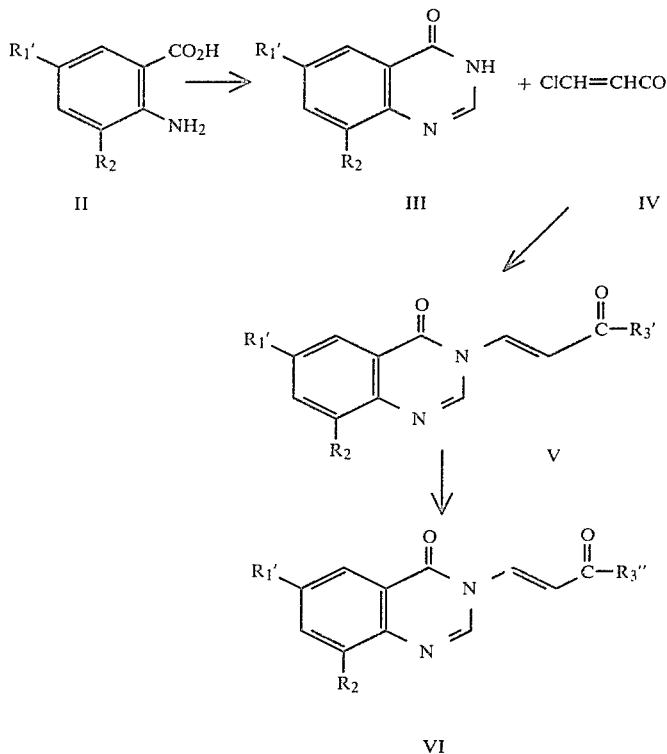

wherein $R_1'$ is hydrogen, lower alkyl, lower cycloalkyl, lower alkoxy, hydroxy, halo, lower alkylthio, di-$(C_1-C_7)$alkyl-$N(CH_2)_nO$— or 2-hydroxyethoxy; $R_2$ is hydrogen, lower alkyl or lower alkoxy; $R'_3$ is lower alkoxy, di-$(C_1-C_7)$alkyl-$N(CH_2)_nO$— or di-$(C_1-C_7)$-alkyl-$N(CH_2)_nNH$—; and $R''_3$ is hydroxy.

In Formula Scheme I, the compound of formula II is converted to the corresponding compound of formula III utilizing formamide at a temperature in the range of from about 120° to about 190° C.; preferably without added solvent. The compounds of formula II are known compounds or can be prepared according to known procedures.

The N-3-alkylation of the compound of formula III with a compound of formula IV, which may be in the trans configuration, i.e.,

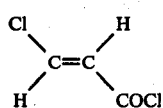

or in the cis configuration, i.e.,

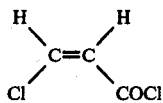

or a mixture thereof [A. N. Kurtz, W. E. Billups, R. B. Greenlee, H. F. Hamil and W. T. Pace, J. Org. Chem., Volume 30, 3141 (1965)] by treatment with an alkanol of the formula

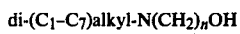   VII or an alkylamine of the formula

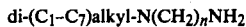   VIII respectively.

The corresponding acid of a compound of formula V can be obtained by hydrolysis of a compound of formula V, wherein $R'_3$ is lower alkoxy. The hydrolysis can be carried out in mineral acid such as hydrochloric acid, and a solvent such as water or acetic acid. Alternatively, compounds of formula V wherein $R'_3$ is di-$(C_1-C_7)$alkyl-$N(CH_2)_nO$—or di-$(C_1-C_7)$alkyl-$N(CH_2)_nNH$—, can be prepared from a compound of formula VI as follows:

The compound of formula VI is converted to the corresponding acid chloride by reaction with thionyl chloride and then treated with a compound of formula VII or a compound of formula VIII, such as 2-(diethylamino)ethanol or 2-(diethylamino)ethylamine, respectively. The compound of formula VI when reacted with a di-$(C_1-C_7)$alkyl-$N(CH_2)_n$ chloride, for example, 2-(diethylamino)ethyl chloride, also yields a compound of formula V, wherein $R'_3$ is di-$(C_1-C_7)$alkyl-$N(CH_2)_nO$—.

The compound of formula VI wherein $R_1'$ is lower alkylthio, $R_2$ is hydrogen and $R_3''$ is hydroxy, can be converted to compounds of the formula

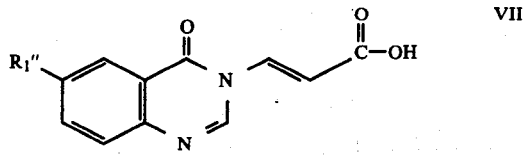   VII wherein $R_1''$ is lower alkylsulfinyl or lower alkylsulfonyl.

More specifically, to obtain a compound of formula VII wherein $R_1''$ is lower alkylsulfinyl, the foregoing lower alkylthio compound of formula VI is oxidized according to known methods, for example, with an alkali metal metaperiodate such as sodium metaperiodate, preferably at room temperature. To obtain a compound of formula VII wherein $R_1''$ is lower alkylsulfonyl, the foregoing lower alkylthio compound of formula VI is oxidized according to known methods, for example, with hydrogen peroxide in the presence of a lower alkanoic acid such as acetic acid, preferably at a temperature in the range of from about 50° to about 100° C. The products of formula V and/or formula VI or those prepared from the compound of formula V wherein $R'_3$ is alkoxy, or the compounds of formula VII, can be separated and recovered by conventional methods such as crystallization, and the like.

The compounds of formula I, wherein $R_3$ is hydroxy, form salts with pharmaceutically acceptable bases. Exemplary of such bases are alkali metal hydroxides, such as sodium hydroxide, potassium hydroxide, and the like; alkaline earth hydroxides, such as calcium hydroxide, barium hydroxide, and the like; sodium alkoxides, such as sodium ethanolate, potassium ethanolate, and the like; organic bases such as piperidine, diethylamine, N-methylglucamine, N-(2-aminoethyl)glycine, and the like.

The compounds of formula I, wherein $R_3$ is di-$(C_1-C_7)$alkyl-$N(CH_2)_nO$— or di-$(C_1-C_7)$alkyl-$N(CH_2)_nNH$—, form salts with pharmaceutically acceptable acids. Exemplary of such acids are both pharmaceutically acceptable organic and inorganic acids, such as methanesulfonic acid, p-toluenesulfonic acid, hydrochloric acid, hydrobromic acid, sulfuric acid, or the like.

The compounds of formula I as well as their pharmaceutically acceptable salts inhibit cutaneous anaphylaxis in rats, and are therefore useful in the prevention of allergic reactions, for example, they are useful in the prophylactic treatment of bronchial asthma. The antianaphylactic activity can be demonstrated by the passive cutaneous anaphylaxis assay (PCA Test) in the rat. This test involves passive local sensitization of rats by intra-dermal injection of anti-sera. After a latent period of 24 hours, the test compound, in this case, a trans-3-(4-oxo-4H-quinazolin-3-yl)-2-propenoic acid, is given intraperitoneally followed after 5 minutes by an intravenous injection of reagen and Evans blue dye. The events associated with localized antigen-antibody reaction lead to the formation of skin wheals whose sizes are measured. The ability of the test compound to decrease the size of the wheals compared to controls is taken as a measure of its activity.

When compounds of the invention, such as trans-3-(6-isopropyl-4-oxo-4H-quinazolin-3-yl)-2-propenoic acid or trans-3-[6-(methylthio)-4-oxo-4H-quinazolin-3-yl]2-propenoic acid, are utilized as the test compounds at a dose of 16 mg/kg intraperitoneally, the reduction in the wheal size is 100% and 87%, respectively.

The anti-allergic activity can also be demonstrated in the passively sensitized rat (IgE). In this test, a rat is administered anti-sera intravenously 18 hours prior to the intravenous antigen (egg albumin) challenge. The antigen challenge originates the Immediate Hypersensitivity Reaction (IHR). When an anti-allergic compound is administered intravenously prior to the antigen challenge, it inhibits IHR and prevents bronchospasm.

When trans-3-[6-(methylthio)-4-oxo-4H-quinazolin-3-yl]-2-propenoic acid is utilized in the foregoing test at an oral dose of 0.02 mg/kg, the percent inhibition of bronchospasm is 50%.

The compounds of formula I and their pharmaceutically acceptable salts can be administered orally or parenterally as anti-allergic agents, for example in the prophylactic treatment of bronchial asthma, with dosage adjustments for individual requirements. They can be administered therapeutically, for example, orally or parenterally, by incorporating a therapeutic dosage in a conventional dosage form, such as tablets, capsules, elixirs, suspensions, solutions or the like. They can be administered in mixture with conventional pharmaceutical carriers or excipients, such as, for example, corn starch, calcium stearate, magnesium carbonate, calcium silicate, dicalcium phosphate, talc, lactose, and the like. Moreover, they can be administered in the presence of buffers, or agents used to adjust to isotonicity, and the pharmaceutical dosage forms can, if desired, be subjected to conventional pharmaceutical expedients such as, for example, sterilization. As stated above, the dosage can be adjusted to individual requirements. They can also contain other therapeutically valuable substances.

The quantity of active medicament which is present in any of the above-described dosage forms is variable. It is preferred, however, to provide capsules or tablets containing from about 1 mg. to about 25 mg. of the formula I base or an equivalent amount of a medicinally acceptable salt thereof.

The frequency with which any such dosage form will be administered to a patient will vary, depending upon the quantity of active medicament present therein and the needs and requirements of the patient. Under ordinary circumstances, however, up to about 100 mg. of the compound can be administered daily in several dosages. It is to be understood, however, that the dosages set forth therein are exemplary only and that they do not, to any extent, limit the scope or practice of this invention.

The Examples which follow further illustrate the invention. All temperatures are stated in degrees Centigrade unless otherwise mentioned.

EXAMPLE 1

Preparation of trans-3-(6-methoxy-4-oxo-4H-quinazolin-3-yl)-2-propenoic acid methyl ester 1.284 g. of a 57% oil dispersion of sodium hydride was washed free of oil with pentane and then suspended in 25 ml. of anhydrous dimethylformamide. While maintaining an argon atmosphere, 4.00 g. of 6-methoxy-4(3H)-quinazolinone [B. R. Baker, R. E. Schaub, J. P. Joseph, F. J. McEvoy and J. H. Williams, J. Org. Chem., 17, 141 (1952)] was added. The reaction mixture was stirred 10 minutes at room temperature and 30 minutes at 50°. After cooling to 30°, 3.02 g. of methyl trans-3-chloroacrylate [H. O. House, W. L. Roelofs and B. M. Trost, J. Org. Chem., 31, 646 (1966)] in 20 ml. of anhydrous dimethylformamide was added dropwise. The reaction mixture was then heated at 50° for 1 hour, cooled in an ice bath and 100 ml. of water was added. The resultant solid was filtered and recrystallized from methylene chloride-methanol to yield 4.30 g, mp 184°–186°, of pure trans-3-(6-methoxy-4-oxo-4H-quinazolin-3-yl)-2-propenoic acid methyl ester.

EXAMPLE 2

Preparation of trans-3-(6-methoxy-4-oxo-4H-quinazolin-3-yl)-2-propenoic acid

A mixture of 4.30 g. of trans-3-(6-methoxy-4-oxo-4H-quinazolin-3-yl)-2-propenoic acid methyl ester and 110 ml. of 6 N hydrochloric acid was stirred and refluxed for 15 minutes. 100 Ml. of water was added and the reaction mixture was cooled in an ice bath and the resultant solid was filtered to yield 3.13 g, mp 298°–299°, of pure trans-3-(6-methoxy-4-oxo-4H-quinazolin-3-yl)-2-propenoic acid.

EXAMPLE 3

Preparation of trans-3-(6-methoxy-4-oxo-4H-quinazolin-3-yl)-2-propenoic acid sodium salt hemihydrate To a suspension of 0.862 g. of trans-3-(6-methoxy-4-oxo-4H-quinazolin-3-yl)-2-propenoic acid in 15 ml. of water was added 3.5 ml. of 1.0 N sodium hydroxide with stirring. After a few minutes, the mixture was filtered and 100 ml. of pyridine was added to the filtrate. The solution was boiled to remove most of the water and allowed to cool. Filtration gave 0.68 g, mp 329°–330°, of pure trans-3-(6-methoxy-4-oxo-4H-quinazolin-3-yl)-2-propenoic acid sodium salt hemihydrate.

EXAMPLE 4

Preparation of trans-3-(6-methoxy-4-oxo-4H-quinazolin-3-yl)-2-propenoic acid, N-(2-aminoethyl)glycine salt To a solution of 0.513 g. of trans-3-(6-methoxy-4-oxo-4H-quinazolin-3-yl)-2-propenoic acid in 35 ml. of pyridine was added 0.248 g. of N-(2-aminoethyl) glycine dissolved in 5 ml. of water. The solution was concentrated in vacuo and the residue was taken up in 150 ml. of water containing 3 ml. of pyridine. This solution was lyophilized to give trans-3-(6-methoxy-4-oxo-4H-quinazolin-3-yl)-2-propenoic acid, N-(2-aminoethyl)glycine salt.

EXAMPLE 5

Preparation of trans-3-(6-methoxy-4-oxo-4H-quinazolin-3-yl)-2-propenoic acid (2-diethylaminoethyl) ester hydrochloride A suspension of 1.65 g. of trans-3-(6-methoxy-4-oxo-4H-quinazolin-3-yl)-2-propenoic acid in 100 ml. of isopropyl alcohol was stirred and heated at reflux during the dropwise addition of 2.7 g. of 2-(diethylamino)ethyl chloride in 30 ml. of isopropyl alcohol. The reaction mixture was stirred and refluxed for 8 hours and then allowed to cool to room temperature. The precipitate was filtered and then treated with 125 ml. of saturated sodium bicarbonate solution and extracted with chloroform. The dried magnesium sulfate extract was concentrated in vacuo to yield 2.3 g. of solid. This solid was dissolved in 35 ml. of methylene chloride and treated with 2.53 ml. of 2.65 N hydrochloric acid in methanol. Ether was added to turbidity and the solution was cooled overnight. Filtration gave 1.30 g, mp 217°–218°, of pure trans-3-(6-methoxy-4-oxo-4H-quinazolin-3-yl)-2-propenoic acid (2-diethylaminoethyl) ester hydrochloride.

EXAMPLE 6

Preparation of 6-isopropyl-4(3H)quinazolinone

A mixture of 5.38 g. of 5-isopropylanthranilic acid and 4.82 ml. of formamide was heated at 140°–145° with stirring for 4 hours and then cooled to room temperature. The excess formamide was removed in vacuo and water was added. The precipitate was filtered and recrystallized from methylene chloride-hexane to yield 4.50 g, mp 147°, of pure 6-isopropyl-4(3H)quinazolinone.

EXAMPLE 7

Preparation of trans-3-(6-isopropyl-4-oxo-4H-quinazolin-3-yl)-2-propenoic acid methyl ester 1.15 g. of a 57% oil dispersion of sodium hydride was washed free of oil with pentane and then suspended in 25 ml. of anhydrous dimethylformamide. While maintaining an argon atmosphere, 3.86 g. of 6-isopropyl-4(3H)quinazolinone was added. The reaction mixture was stirred for 30 minutes at room temperature and 1 hour at 50°. After cooling to 30°, 2.68 g. of methyl trans-3-chloroacrylate in 10 ml. of anhydrous dimethylformamide was added dropwise. The reaction mixture was then heated at 50° for 1.5 hours and concentrated in vacuo to remove most of the dimethylformamide. Water was added and the resultant solid was filtered and recrystallized from methylene chloride-methanol to give 2.73 g, mp 145°, of pure trans-3-(6-isopropyl-4-oxo-4H-quinazolin-3-yl)-2-propenoic acid methyl ester.

EXAMPLE 8

Preparation of trans-3-(6-isopropyl-4-oxo-4H-quinazolin-3-yl)-2-propenoic acid

A mixture of 2.995 g. of trans-3-(6-isopropyl)-4-oxo-4H-quinazolin-3-yl)-2-propenoic acid methyl ester and 175 ml. of 6 N hydrochloric acid was stirred and refluxed for 20 minutes. After cooling to room temperature, 175 ml. of water was added and the reaction mixture was cooled overnight. Filtration gave 1.58 g, mp 245°, of pure trans3-(6-isopropyl-4-oxo-4H-quinazolin-3-yl)-2-propenoic acid.

EXAMPLE 9

Preparation of trans-3-(6-isopropyl-4-oxo-4H-quinazolin-3-yl)-2-propenoic acid sodium salt 0.25 molar hydrate To a suspension of 1.29 g. of trans-3-(6-isopropyl-4-oxo-4H-quinazolin-3-yl)-2-propenoic acid in 20 ml. of water was added 5.0 ml. of 1.0 N sodium hydroxide with stirring. After a few minutes, the mixture was filtered and 50 ml. of water was added to the filtrate. This solution was lyophilized to yield 1.40 g. of trans-3-(6-isopropyl-4-oxo-4H-quinazolin-3-yl)-2-propenoic acid sodium salt 0.25 molar hydrate.

EXAMPLE 10

Preparation of trans-3-(6-isopropyl-4-oxo-4H-quinazolin-3-yl)-2-propenoic acid, N-(2-aminoethyl)glycine salt To a solution of 0.774 g. of trans-3-(6-isopropyl-4-oxo-4H-quinazolin-3-yl)-2-propenoic acid in 50 ml. of pyridine was added 0.354 g. of N-(2-aminoethyl)glycine in 5 ml. of water. The solution was concentrated in vacuo, and the residue was taken up in 50 ml. of water containing a few drops of pyridine. This solution was lyophilized to give trans-3-(6-isopropyl-4-oxo-4H-quinazolin-3-yl)-2-propenoic acid, N-(2-aminoethyl)glycine salt.

EXAMPLE 11

Preparation of 6-cyclopropyl-4(3H)quinazlinone

A mixture of 1.77 g. of 5-cyclopropylanthranilic acid and 1.6 ml. of formamide was heated at 140°-145° with stirring for 4 hours and then cooled to room temperature. The excess formamide was removed in vacuo and water was added. The precipitate was filtered and recrystallized from methanol-ethyl acetate to yield 1.40 g, mp 201°-202°, of pure 6-cyclopropyl-4(3H)quinazolinone.

EXAMPLE 12

Preparation of trans-3-(6-cyclopropyl-4-oxo-4H-quinazolin-3-yl)-2-propenoic acid methyl ester 0.395 g. of a 57% oil dispersion of sodium hydride was washed free of oil with pentane and then suspended in 25 ml. of anhydrous dimethylformamide. While maintaining an argon atmosphere, 1.40 g. of 6-cyclopropyl-4(3H)quinazolinone was added. The reaction mixture was stirred at room temperature for 15 minutes and at 50° for 30 minutes. After cooling to 30°, 1.00 g. of methyl trans-3-chloro-acrylate in 5 ml. of anhydrous dimethylformamide was added dropwise. The reaction mixture was then heated at 50° for 75 minutes and concentrated in vacuo to remove most of the dimethylformamide. Water was added and the resultant solid was filtered and recrystallized from methylene chloride-methanol to give 1.24 g, mp 178°, of pure trans3-(6-cyclopropyl-4-oxo-4H-quinazolin-3-yl)-2-propenoic acid methyl ester.

EXAMPLE 13

Preparation of trans-3-(6-cyclopropyl-4-oxo-4H-quinazolin-3-yl)-2-propenoic acid A mixture of 1.18 g. of trans-3-(6-cyclopropyl-4-oxo-4H-quinazolin-3-yl)-2-propenoic acid methyl ester and 50 ml. of 6 N hydrochloric acid was stirred and refluxed for 13 minutes. After cooling to room temperature, 150 ml. of water was added and the reaction mixture was cooled. Filtration gave the crude product which was recrystallized from pyridine to give 0.38 g, mp 291°-293°, of pure trans-3-(6-cyclopropyl-4-oxo-4H-quinazolin-3-yl)-2-propenoic acid.

EXAMPLE 14

Preparation of trans-3-(6-chloro-4-oxo-4H-quinazolin-3-yl)-2-propenoic acid methyl ester 0.367 g. of a 57% oil dispersion of sodium hydride was washed free of oil with pentane and then suspended in 25 ml. of anhydrous dimethylformamide. While maintaining an argon atmosphere, 1.23 g. of 6-chloro-4(3H)quinazolinone [B. R. Baker, R. E. Schaub, J. P. Joseph, F. J. McEvoy and J. H. Williams, J. Org. Chem., 17, 141 (1952)] was added. The reaction mixture was stirred at room temperature for 15 minutes and at 50° for 30 minutes. After cooling to 30°, 0.91 g. of methyl trans-3-chloroacrylate in 5 ml. of anhydrous dimethylformamide was added dropwise. The reaction mixture was then heated at 50° for 75 minutes and concentrated in vacuo to remove most of the dimethylformamide. Water was added, and the resultant solid was filtered and recrystallized from methylene chloride-methanol to yield 0.95 g, mp 171°-172°, of pure trans-3-(6-chloro-4-oxo-4H-quinazolin-3-yl)-2-propenoic acid methyl ester.

EXAMPLE 15

Preparation of trans-3-(6-chloro4-oxo-4H-quinazolin-3-yl)-2-propenoic acid

A mixture of 0.92 g. of trans-3-(6-chloro-4-oxo-4H-quinazolin-3-yl)-2-propenoic acid methyl ester and 30 ml. of 6 N hydrochloric acid was stirred and refluxed for 15 minutes. After cooling to room temperature, 200 ml. of water was added and the reaction mixture was cooled. Filtration gave the crude product which was recrystallized from pyridine to give 0.31 g, mp 297°–298°, of pure trans-3-(6-chloro-4-oxo-4H-quinazolin-3-yl)-2-propenoic acid.

EXAMPLE 16

Preparation of 6-(methylthio)-4-(3H)quinazolinone

A mixture of 1.97 g. of methyl 5-(methylthio)anthranilate and 1.6 ml. of formamide was heated at 140°–145° with stirring for 4 hours and then at 190° for 4 hours and then cooled to room temperature. The excess formamide was removed in vacuo and water was added. The precipitate was filtered and recrystallized from methanol-ethyl acetate to yield 0.73 g, mp 203°–204.5°, of pure 6-(methylthio)-4(3H)quinazolinone.

EXAMPLE 17

Preparation of trans-3-[6-(methylthio)-4-oxo-4H-quinazolin-3-yl]-2-propenoic acid methyl ester 0.205 g. of a 57% oil dispersion of sodium hydride was washed free of oil with pentane and then suspended in 25 ml. of anhydrous dimethylformamide. While maintaining an argon atmosphere, 0.720 g. of 6-(methylthio)-4(3H)quinazolinone was added. The reaction mixture was stirred at room temperature for 10 minutes and at 50° for 30 minutes. After cooling to 30°, 0.497 g. of methyl trans-3-chloroacrylate in 5 ml of anhydrous dimethylformamide was added dropwise. The reaction mixture was then heated at 50° for 1 hour and concentrated in vacuo to remove most of the dimethylformamide. Water was added and the resultant solid was filtered and recrystallized from methylene chloride-methanol to yield 0.700 g, mp 170°, of pure trans-3-[6-(methylthio)-4-oxo-4H-quinazolin-3-yl]-2-propenoic acid methyl ester.

EXAMPLE 18

Preparation of trans-3-[6-(methylthio)-4-oxo-4H-quinazolin-3-yl]-2-propenoic acid A mixture of 0.65 g. of trans-3-[6-(methylthio)-4-oxo-4H-quinazolin-3-yl]-2-propenoic acid methyl ester and 30 ml. of 6 N hydrochloric acid was stirred and refluxed for 20 minutes. After cooling to room temperature, 100 ml. of water was added and the reaction mixture was cooled. Filtration gave the crude product which was recrystallized from pyridine to yield 0.47 g, mp 271°–272°, of pure trans-3-[6-(methylthio)-4-oxo-4H-quinazolin-3-yl]-2-propenoic acid.

EXAMPLE 19

Preparation of 6-isopropoxy-4(3H)quinazolinone

A mixture of 3.90 g. of 5-isopropoxyanthranilic acid and 3.2 ml. of formamide was heated at 140°–145° for 4 hours and then cooled to room temperature. The excess formamide was removed in vacuo and water was added. The precipitate was filtered and recrystallized from methanol to give 2.99 g, mp 206°–208°, of pure 6-isopropoxy-4(3H)quinazolinone.

EXAMPLE 20

Preparation of trans-3-(6-isopropoxy-4-oxo-4H-quinazolin-3-yl)-2-propenoic acid methyl ester 0.888 g. of a 57% oil dispersion of sodium hydride was washed free of oil with pentane and then suspended in 25 ml. of anhydrous dimethylformamide. While maintaining an argon atmosphere, 3.31 g. of 6-isopropoxy-4(3H)quinazolinone was added. The reaction mixture was stirred at room temperature for 10 minutes and at 50° for 45 minutes. After cooling to 30°, 2.150 g. of methyl trans-3-chloroacrylate in 7 ml. of anhydrous dimethylformamide was added dropwise. The reaction mixture was heated at 50° for 1 hour and concentrated in vacuo to remove most of the dimethylformamide. Water was added and the resultant solid was filtered and recrystallized from methylene chloride-methanol to yield 4.00 g, mp 156.5°–157.5°, of pure trans-3-(6-isopropoxy-4-oxo-4H-quinazolin-3-yl)-2-propenoic acid methyl ester.

EXAMPLE 21

Preparation of trans-3-(6-isopropoxy-4-oxo-4H-quinazolin-3-yl)-2-propenoic acid

A mixture of 1.44 g. of trans-3-(6-isopropoxy-4-oxo-4H-quinazolin-3-yl)-2-propenoic acid methyl ester and 60 ml. of 6 N hydrochloric acid was stirred and refluxed for 5 minutes. After cooling to room temperature, 200 ml. of water was added and the reaction mixture was cooled. Filtration gave the crude product which was recrystallized from acetic acid to give 0.37 g, mp 232.5°–233.5°, of pure trans-3-(6-isopropoxy-4-oxo-4H-quinazolin-3-yl)-2-propenoic acid.

EXAMPLE 22

Preparation of 2-bromo-4,6-diisopropylaniline

To a stirred solution of 30 g. of 2,4-diisopropylaniline [A. Newton, J. Amer. Chem. Soc., 65, 2434 (1943)] in 100 ml. of chloroform was added 10.8 ml. of bromine in 30 ml. of chloroform over a 2 hour period. The reaction temperature was maintained at 16°–24° by periodic cooling. After stirring 30 minutes more, aqueous sodium bicarbonate solution was added until the aqueous layer remained basic. The organic layer was washed with aqueous sodium sulfite solution, dried (magnesium sulfate) and concentrated in vacuo to give 43.0 g. of 2-bromo-4,6-diisopropylaniline as an oil.

EXAMPLE 23

Preparation of 2-cyano-4,6-diisopropylaniline

A mixture of 50 g. of 2-bromo-4,6-diisopropylaniline and 36 g. of cuprous cyanide in 400 ml. of anhydrous dimethylformamide was stirred at reflux for 5 hours. The dimethylformamide was removed in vacuo to yield an oil to which was added 70 ml. of ethylene diamine and 300 ml. of water. This mixture was heated on the steam bath for 10 minutes, cooled and extracted with methylene chloride. The extract was dired over magnesium sulfate, concentrated to a dark oil and chromatographed on 450 g. of silica gel. Elution with 20% ethyl acetate in hexane gave 30 g. of nearly pure 2-cyano-4,6-diisopropylaniline.

EXAMPLE 24

Preparation of 3,5-diisopropylanthranilic acid

A solution of 30 g. of 2-cyano-4,6-diisopropylaniline in 150 ml. of acetic acid and 300 ml. of 50% sulfuric acid was stirred and refluxed for 4 hours. The acetic acid was removed in vacuo and the pH of the aqueous residue was adjusted to 4.0 with concentrated sodium hydroxide with ice cooling. The product was extracted with methylene chloride and the extract was concentrated in vacuo to an oil which was crystallized from hexane to yield 3.9 g, mp 114°–116°, of pure 3,5-diisopropylanthranilic acid.

EXAMPLE 25

Preparation of 6,8-diisopropyl-4(3H)quinazolinone

A mixture of 2.21 g. of 3,5-diisopropylanthranilic acid and 1.6 ml. of formamide was heated at 140°–145° for 4 hours and then cooled to room temperature. The excess formamide was removed in vacuo and water was added. The product was extracted with methylene chloride. The dried extract was concentrated in vacuo to a solid which was recrystallized from methylene chloride-hexane to give 1.12 g, mp 164°–165°, of pure 6,8-diisopropyl-4(3H)quinazolinone.

EXAMPLE 26

Preparation of trans-3-(6,8-diisopropyl-4-oxo-4H-quinazolin-3-yl)-2-propenoic acid methyl ester 0.256 g. of a 57% oil dispersion of sodium hydride was washed free of oil with pentane and then suspended in 20 ml. of anhydrous dimethylformamide. While maintaining an argon atmosphere, 1.08 g. of 6,8-diisopropyl-4(3H)quinazolinone was added. The reaction mixture was stirred at room temperature for 10 minutes and at 50° for 45 minutes. After cooling to 30°, 0.62 g of methyl trans-3-chloroacrylate in 5 ml. of dimethylformamide was added dropwise. The reaction mixture was heated at 50° for 1 hour and concentrated in vacuo to remove most of the dimethylformamide. 100 ml. of water was added and the product was extracted with methylene chloride. The dried magnesium sulfate extract was concentrated in vacuo to yield an oil which gradually crystallized. Recrystallization from methanol gave 1.20 g, mp 102°–103°, of pure trans-3-(6,8-diisopropyl-4-oxo-4H-quinazolin-3-yl)-2-propenoic acid methyl ester.

EXAMPLE 27

Preparation of trans-3-(6,8-diisopropyl-4-oxo-4H-quinazolin-3-yl)-2-propenoic acid A mixture of 1.15 g. of trans-3-(6,8-diisopropyl-4-oxo-4H-quinazolin-3-yl)-2-propenoic acid methyl ester and 50 ml. of 6 N hydrochloric acid was stirred and refluxed for 20 minutes. After cooling to room temperature, 100 ml. of water was added and the reaction mixture was cooled and filtered to yield 0.60 g, mp 181°–182° of pure trans-3-(6,8-diisopropyl-4-oxo-4H-quinazolin-3-yl)-2-propenoic acid.

EXAMPLE 28

Preparation of trans-3-(8-methoxy-4-oxo-4H-quinazolin-3-yl)-2-propenoic acid methyl ester 0.125 g. of a 57% oil dispersion of sodium hydride was washed free of oil with hexane and then suspended in 5 ml. of anhydrous dimethylformamide. While maintaining an argon atmosphere, 0.400 g. of 8-methoxy-4(3H)-quinazolinone [Iyer, Anand and Dhar, *J. Sci. Ind. Res. India*, 15C, 1 (1956)] was added. The reaction mixture was stirred 10 minutes at room temperature and 45 minutes at 50°. After cooling to 30°, 0.300 g. of methyl trans-3-chloroacrylate in 5 ml. of anhydrous dimethylformamide was added dropwise. The reaction mixture was then heated at 50° for 1.5 hours, cooled and concentrated in vacuo to remove most of the dimethylformamide. Water was added and the product was extracted with methylene chloride. The extract was concentrated in vacuo and the resultant solid was crystallized from chloroform-methanol to give 0.337 g, mp 203°–208°, of pure trans-3-(8-methoxy-4-oxo-4H-quinazolin-3-yl)-2-propenoic acid methyl ester.

EXAMPLE 29

Preparation of trans-3-(8-methoxy-4-oxo-4H-quinazolin-3-yl)-2-propenoic acid

A mixture of 0.320 g. of trans-3-(8-methoxy-4-oxo-4H-quinazolin-3-yl)-2-propenoic acid methyl ester and 15 ml. of 6 N hydrochloric acid was stirred and refluxed for 15 minutes. After cooling to room temperature, 15 ml. of water was added and after cooling the resultant solid was filtered to yield 0.164 g, mp 289°–291°, of pure trans-3-(8-methoxy-4-oxo-4H-quinazolin-3-yl)-2-propenoic acid.

EXAMPLE 30

Preparation of 6,8-dimethoxy-4(3H)-quinazolinone

A mixture of 1.97 g. of 3,5-dimethoxyanthranilic acid and 1.6 ml. of formamide was stirred and heated at 150° for 5 hours and then at 165° for 11 hours. After cooling, water was added and the product was filtered. Recrystallization from methanol gave 0.76 g, mp 280°–282°, of pure 6,8-dimethoxy-4(3H)-quinazolinone.

EXAMPLE 31

Preparation of trans-3-(6,8-dimethoxy-4-oxo-4H-quinazolin-3-yl)-2-propenoic acid methyl ester 0.189 g. of a 57% oil dispersion of sodium hydride was washed free of oil with hexane and then suspended in 10 ml. of anhydrous dimethylformamide. While maintaining an argon atmosphere, 0.712 g. of 6,8-dimethoxy-4(3H)-quinazolinone was added. The reaction mixture was stirred at room temperature for 5 minutes and at 50° for 45 minutes. After cooling to 30°, 0.459 g. of methyl trans-3-chloroacrylate in 5 ml. of anhydrous dimethylformamide was added dropwise. The reaction mixture was then heated at 50° for 1.5 hours and concentrated in vacuo to remove most of the dimethylformamide. Water was added and the product was extracted with methylene chloride. The dried (magnesium sulfate)extract was concentrated in vacuo to a solid which was recrystallized from chloroform-methanol to give 0.794 g, mp 224°–226°, of pure trans-3-(6,8-dimethoxy-4-oxo-4H-quinazolin-3-yl)-2-propenoic acid methyl ester.

EXAMPLE 32

Preparation of trans-3-(6,8-dimethoxy-4-oxo-4H-quinazolin-3-yl)-2-propenoic acid A mixture of 0.745 g. of trans-3-(6,8-dimethoxy-4-oxo-4H-quinazolin-3-yl)-2-propenoic acid methyl ester and 30 ml. of 6 N hydrochloric acid was stirred and refluxed for 15 minutes. After cooling, 30 ml. of water was added and the resultant solid was filtered. Recrystallization from acetic acid and then from pyridine gave 0.398 g, mp 305°–307°, of pure trans-3-(6,8-dimethoxy-4-oxo-4H-quinazolin-3-yl)-2-propenoic acid.

EXAMPLE 33

Preparation of trans-3-(6,8-dimethyl-4-oxo-4H-quinazolin-3-yl)-2-propenoic acid methyl ester 0.380 g. of a 57% oil dispersion of sodium hydride was washed free of oil with hexane and then suspended in 20 ml. of anhydrous dimethylformamide. While maintaining an argon atmosphere, 1.20 g. of 6,8-dimethyl-4(3H)-quinazolinone [B. R. Baker, R. E. Schaub, J. P. Joseph, F. J. McEvoy and J. H. Williams, *J. Org. Chem.*, 17, 149 (1952)] was added. The reaction mixture was stirred for 10 minutes at room temperature and for 1 hour at 50°. After cooling to 30°, 0.916 g. of methyl trans-3-chloroacrylate in 10 ml. of anhydrous dimethylformamide was added dropwise. The reaction mixture was then heated at 50° for 1.5 hours and concentrated in vacuo to remove most of the dimethylformamide. Water was added and the resultant solid was filtered and recrystallized from chloroform-methanol to yield 1.42 g, mp 139°–141°, of pure trans-3-(6,8-dimethyl-4-oxo-4H-quinazolin-3-yl)-2-propenoic acid methyl ester.

EXAMPLE 34

Preparation of trans-3-(6,8-dimethyl-4-oxo-4H-quinazolin-3-yl)-2-propenoic acid

A mixture of 1.32 g. of trans-3-(6,8-dimethyl-4-oxo-4H-quinazolin-3-yl)-2-propenoic acid methyl ester and 60 ml. of 6 N hydrochloric acid was stirred and refluxed for 15 minutes. After cooling, 60 ml. of water was added and the solid product was filtered to yield 1.10 g, mp 284°–288°, of pure trans-3-(6,8-dimethyl-4-oxo-4H-quinazolin-3-yl)-2-propenoic acid.

EXAMPLE 35

Preparation of 6-(2-diethylaminoethoxy)-4(3H)-quinazolinone hydrochloride

A mixture of 1.00 g. of 5-(2-diethylaminoethoxy)anthranilic acid dihydrochloride and 1 ml. of formamide was heated at 150° with stirring for 7 hours. The excess formamide was removed in vacuo and the residue was triturated with methanol-ether to give 0.81 g. of solid. Recrystallization from isopropyl alcohol-water gave 0.33 g, mp 233°–234°, of pure 6-(2-diethylaminoethoxy)-4(3H)-quinazolinone hydrochloride.

EXAMPLE 36

Preparation of trans-3-[6-(2-diethylaminoethoxy)-4-oxo-4H-quinazolin-3-yl]-2-propenoic acid methyl ester 0.20 g. of a 57% oil dispersion of sodium hydride was washed free of oil with hexane and then suspended in 25 ml. of anhydrous dimethylformamide. While maintaining an argon atmosphere, 0.94 g. of 6-(2-diethylaminoethoxy)-4(3H)-quinazolinone was added. The reaction mixture was stirred for 15 minutes at room temperature and for 1 hour at 50°. After cooling to 30°, 0.48 g. of methyl trans-3-chloroacrylate in 5 ml. of anhydrous dimethylformamide was added dropwise. The reaction mixture was then heated at 50° for 1 hour 45 minutes and concentrated in vacuo to remove most of the dimethylformamide. Water was added and the resultant solid was filtered to give 1.10 g, mp 131°–133°, of pure trans-3-[6-(2-diethylaminoethoxy)-4-oxo-4H-quinazolin-3-yl]-2-propenoic acid methyl ester.

EXAMPLE 37

Preparation of trans-3-[6-(2-diethylaminoethoxy)-4-oxo-4H-quinazolin-3-yl]-2-propenoic acid hydrochloride A mixture of 1.0454 g. of trans-3-[6-(2-diethylaminoethoxy)-4-oxo-4H-quinazolin-3-yl]-2-propenoic acid methyl ester and 25 ml. of 6 N hydrochloric acid was stirred and refluxed for 20 minutes. After concentration in vacuo to a yellow solid, this was recrystallized from isopropyl alcohol-water to yield 0.69 g, mp 227°–230°, of pure trans-3-[6-(2-diethylaminoethoxy)-4-oxo-4H-quinazolin-3-yl]-2-propenoic acid hydrochloride.

EXAMPLE 38

Preparation of 6-(2-hydroxyethoxy)-4(3H)-quinazoline

A mixture of 1.74 g. of 5-(2-hydroxyethoxy)anthranilic acid and 2 ml. of formamide was heated at 150° with stirring for 7.5 hours. Water was added and the product was filtered and crystallized from methanol to yield 1.24 g, mp 200°–202°, of pure 6-(2-hydroxyethoxy)-4(3H)-quinazolinone.

EXAMPLE 39

Preparation of trans-3-[6-(2-hydroxyethoxy)-4-oxo-4H-quinazolin-3-yl]-2-propenoic acid To 2.0479 g. of 6-(2-hydroxyethoxy)-4(3H)-quinazolinone in 60 ml. of anhydrous dimethylformamide was added 1.52 ml. of triethylamine followed by 1.40 ml. of trimethylsilyl chloride added dropwise. After stirring at 25° for 1.5 hours, the precipitated triethylamine hydrochloride was removed by filtration. The filtrate was added to 0.6430 g. of 57% sodium hydride which had previously been washed with hexane to remove the oil. After stirring for 5 minutes in an argon atmosphere, the reaction mixture was heated at 50° for 45 minutes. On cooling to 30°, 1.3560 g. of methyl trans-3-chloroacrylate in 2 ml. of dimethylformamide was added dropwise. The reaction mixture was then heated at 50° for 75 minutes and concentrated in vacuo to remove most of the dimethylformamide. Hydrochloric acid (50 ml. of 6 N) was added and the mixture was stirred and refluxed for 15 minutes. After cooling, the resultant solid was filtered, washed well with water and dried to yield 0.9607 g, mp 247°–248°, of pure trans-3-[6-(2-hydroxyethoxy)-4-oxo-4H-quinazolin-3-yl]-2-propenoic acid.

EXAMPLE 40

Preparation of trans-3-(4-oxo-4H-quinazolin-3-yl)-2-propenoic acid methyl ester 0.750 g. of a 57% oil dispersion of sodium hydride was washed free of oil with hexane and then suspended in 40 ml. of anhydrous dimethylformamide. While maintaining an argon atmosphere, 2.000 g. of 4(3H)-quinazolinone [W. L. F. Armarego, *J. Appl. Chem.*, 11, 70 (1961)] was added. The reaction mixture was stirred and heated at 50° for 1 hour. After cooling to 25°, 1.800 g. of methyl trans-3-chloroacrylate in 20 ml. of anhydrous dimethylformamide was added dropwise. The reaction mixture was then stirred and heated at 50° for 1.5 hours, cooled and concentrated on the oil pump. Water was added and the resultant solid was filtered and recrystallized from methylene chloride-ether to give 1.97 g., m.p. 173°–174° of pure trans-3-(4-oxo-4H-quinazolin-3-yl)-2-propenoic acid methyl ester.

EXAMPLE 41

Preparation of trans-3-(4-oxo-4H-quinazolin-3-yl)-2-propenoic acid

A mixture of 1.767 g. of trans-3-(4-oxo-4H-quinazolin-3-yl)-2-propenoic acid methyl ester and 75 ml. of 6 N hydrochloric acid was stirred and refluxed for 15 minutes. After cooling, 100 ml. of water was added and the mixture was cooled in an ice bath. Filtration gave 1.022 g., mp 250°–254°, of pure trans-3-(4-oxo-4H-quinazolin-3-yl)-2-propenoic acid.

EXAMPLE 42

Preparation of trans-3-(6-isopropyl-4-oxo-4H-quinazolin-3-yl)-2-propenoic acid, 2-(diethylamino)ethyl amide hydrochloride A suspension of 1.60 g. of trans-3-(6-isopropyl-4-oxo-4H-quinazolin-3-yl)-2-propenoic acid in 20 ml. of thionyl chloride was stirred and refluxed for 3 hours. The reaction mixture was concentrated in vacuo, toluene was added, and it was concentrated again to remove traces of thionyl chloride. The acid chloride was dissolved in 50 ml. of toluene and 1.08 g. of 2-(diethylamino)ethyl amine in 15 ml. of toluene was added dropwise. The reaction mixture was refluxed for 4 hours and concentrated in vacuo to remove the toluene. After partitioning between ethyl acetate and excess saturated sodium bicarbonate solution, the organic layer was dried (magnesium sulfate) and concentrated to yield a dark oil. Crystallization from hexane gave a gray solid, which was dissolved in 10 ml. of methylene chloride and treated with 2 ml. of 4 N hydrochloric acid in methanol. The solution was concentrated in vacuo and the residue was crystallized from isopropyl alcohol-ether to yield 0.90 g., mp 179°–180°, of trans-3-(6-isopropyl-4-oxo-4H-quinazolin-3-yl)-2-propenoic acid, 2-(diethylamino)ethyl amide hydrochloride.

EXAMPLE 43

Preparation of trans-3-(6,8-diisopropyl-4-oxo-4H-quinazolin-3-yl)-2-propenoic acid, 2-(diethylamino)ethyl ester maleate A suspension of 1.42 g. of trans-3-(6,8-diisopropyl-4-oxo-4H-quinazolin-3-yl)-2-propenoic acid and 1.36 g. of 2-(diethylamino)ethyl chloride in 150 ml. of isopropyl alcohol was stirred and heated at reflux for 16 hours. The reaction mixture was concentrated in vacuo and then partitioned between methylene chloride and saturated sodium bicarbonate solution. The methylene chloride layer was dried (sodium sulfate) and concentrated in vacuo to yield 1.20 g. of an oil. The oil was dissolved in 5 ml. of methylene chloride and treated with a solution of 0.35 g. of maleic acid in 25 ml. of ether. After concentration in vacuo, the residue was crystallized from isopropyl alcohol-ether to give trans-3-(6,8-diisopropyl-4-oxo-4H-quinazolin)-3-yl)-2-propenoic acid, 2-(diethylamino)ethyl ester maleate, mp 81°–83°.

EXAMPLE 44

Preparation of trans-3-(6-isopropyl-4-oxo-4H-quinazolin-3-yl)-2-propenoic acid, 2-(diethylamino)ethyl ester hydrochloride A suspension of 1.55 g. of trans-3-(6-isopropyl-4-oxo-4H-quinazolin-3-yl)-2-propenoic acid in 100 ml. of isopropyl alcohol was stirred and heated at reflux during the dropwise addition of 2.71 g. of 2-(diethylamino)ethyl chloride in 30 ml. of isopropyl alcohol. The reaction mixture was stirred at reflux for 8 hours, filtered, and the solid was washed well with isopropyl alcohol. The filtrate was concentrated to dryness in vacuo and the solid residue was partitioned between chloroform and saturated sodium bicarbonate solution. The chloroform layer was dried (magnesium sulfate) and concentrated in vacuo to yield 2.5 g. of an oil. The oil was dissolved in 35 ml. of methylene chloride and 4.0 ml. of 1.77 N hydrochloric acid in methanol was added. Ether was added to turbidity and the resultant product was filtered to yield 1.88 g., mp 167°–168°, of trans-3-(6-isopropyl-4-oxo-4H-quinazolin-3-yl)-2-propenoic acid, 2-(diethylamino)ethyl ester hydrochloride.

EXAMPLE 45

Preparatios of trans-3-chloroacrylic acid, 2-(diethylamino)ethyl ester

To a stirred solution of 4.00 g. of trans-3-chloroacrylyl chloride [A. N. Kurtz, W. E. Billups, R. B. Greenlee, H. F. Hamil and W. T. Pace, *J. Org. Chem.*, 30, 3141, (1965)] in 10 ml. of methylene chloride was added dropwise 3.78 g. of 2-(diethylamino)ethanol in 5 ml. of methylene chloride. The solution was stirred at room temperature for three days and then washed with saturated sodium bicarbonate solution. After drying (magnesium sulfate), concentration in vacuo gave an oil which was distilled at 110°–130°/1 mm to give 1.63 g. of trans-3-chloroacrylic acid, 2-(diethylamino)ethyl ester.

EXAMPLE 46

Preparation of trans-(6-isopropyl-4-oxo-4H-quinazolin-3-yl)-2-propenoic acid methyl ester using methyl cis-3-chloroacrylate Sodium hydride (0.274 g. of 57% oil dispersion) was washed free of oil with pentane and then suspended in 10 ml. of anhydrous dimethylformamide. While maintaining an argon atmosphere, 0.941 g. of 6-isopropyl-4(3H)-quinazolinone was added. The reaction mixture was then stirred and heated at 50° for 30 minutes. After cooling to room temperature, 0.663 g. of methyl cis-3- chloroacrylate [H. O. House, W. L. Roelofs and B. M. Trost, J. Org. Chem., 31, 646 (1966)] in 5 ml. of dimethylformamide was added dropwise. The reaction mixture was then stirred and heated at 50° for 75 minutes and concentrated in vacuo to remove most of the dimethylformamide. Water was added and the resultant solid was recrystallized from methylene chloride-methanol to give 0.58 g., m.p. 144°-145°, of trans-(6-isopropyl-4-oxo-4H-quinazolin-3-yl)-2-propenoic acid methyl ester.

EXAMPLE 47

Preparation of trans-3-(6-hydroxy-4-oxo-4H-quinazolin-3-yl)-2-propenoic acid methyl ester To 2.726 g. of 6-hydroxy-4(3H)-quinazolinone in 110 ml. of anhydrous dimethylformamide was added 2.6 ml. of triethylamine followed by 2.6 ml. of trimethylchlorosilane. After stirring at room temperature for 2 hours, the triethylamine hydrochloride was removed by filtration. The filtrate was added in one portion to 1.06 g. of a 57% oil dispersion of sodium hydride which had previously been freed of oil by washing with pentane. The reaction mixture was stirred and heated at 50° for 90 minutes. After cooling to room temperature, 2.02 g. of methyl trans-3-chloroacrylate in 10 ml. of dimethylformamide was added dropwise. The reaction mixture was then heated at 50° for 2 hours. The dimethylformamide was removed in vacuo and water was added to yield a solid which was filtered. Recrystallization from ethyl acetate-methanol gave 2.725 g., m.p. 252°-256°, of trans-3-(6-hydroxy-4-oxo-4H-quinazolin-3-yl)-2-propenoic acid methyl ester.

EXAMPLE 48

Preparation of trans-3-(6-hydroxy-4-oxo-4H-quinazolin-3-yl)-2-propenoic acid

A mixture of 8.35 g. of trans-3-(6-hydroxy-4-oxo-4H-quinazolin-3-yl)-2-propenoic acid methyl ester and 500 ml. of 6 N hydrochloric acid was stirred and refluxed for 15 minutes. After cooling, water was added and the resultant solid was filtered to yield 6.33 g., m.p. 294°-296°; of trans-3-hydroxy-4-oxo-4H-quinazolin-3-yl)-2-propenoic acid.

EXAMPLE 49

Preparation of trans-3-[6-(methylsulfinyl)-4-oxo-4H-quinazolin-3-yl]-2-propenoic acid To a stirred suspension of 1.823 g. of trans-3-[6-(methylthio)-4-oxo-4H-quinazolin-3-yl]-2-propenoic acid in 80 ml. of water and 7.7 ml. of 1 N sodium hydroxide at room temperature was added 1.827 g. of sodium metaperiodate. After stirring at room temperature for 4.5 hours, 5 ml. of acetic acid was added and the solid was filtered after stirring for 15 minutes. The crude product was recrystallized twice from acetic acid to give 1.102 g., mp 275°-276°, of pure trans-3-[6-(methylsulfinyl)-4-oxo-4H-quinazolin-3-yl]-2-propenoic acid.

EXAMPLE 50

Preparation of trans-3-[6-(methylsulfonyl)-4-oxo-4H-quinazolin-3-yl]-2-propenoic acid To a stirred suspension of 1.8845 g. of trans-3-[6-(methylthio)-4-oxo-4H-quinazolin-3-yl]-2-propenoic acid in 100 ml. of acetic acid was added 1.63 ml. of 30% hydrogen peroxide. The reaction mixture was stirred and heated at 50° for 3 hours, cooled to room temperature and filtered. Recrystallization from acetic acid gave 0.8097 g., mp 284°-290°, of pure trans-3-[6-(methylsulfonyl)-4-oxo-4H-quinazolin-3-yl]-2-propenoic acid.

EXAMPLE 51

Preparation of trans-N-[2-bis(1-methylethyl)aminoethyl]-3-[6-(1-methylethyl)-4-oxo-4H-quinazolin-3-yl]-2-propenamide hydrochloride A solution of 1.8120 g. of trans-3-[6-(methylethyl)-4-oxo-4H-quinazolin-3-yl]-2-propenoic acid in 30 ml. of thionyl chloride was stirred and refluxed for 2 hours. The excess thionyl chloride was removed in vacuo and dry toluene was added and again concentrated in vacuo to yield the solid acid chloride. Anhydrous dimethylformamide (30 ml.) was added followed by 2.4 ml. of 2-[di(1-methylethyl)amino]ethyl amine at room temperature. The reaction mixture was stirred for 2 hours and left at room temperature for 16 hours. The solvent was removed on the oil pump to yield a dark oil which was dissolved in 20 ml. of methanol and treated with 1.6 ml. of 4.4 N hydrogen chloride in methanol. After removal of the methanol in vacuo, the residue was triturated with isopropyl alcohol-ether and the resultant solid was removed by filtration. Recrystallization from methylene chloride-ether gave 1.3037 g., mp 209°-213°, of pure trans-N-[2-bis(1-methylethyl)aminoethyl]-3-[6-(1-methylethyl)-4-oxo-4H-quinazolin-3-yl]-2-propenamide hydrochloride.

EXAMPLE 52

Tablet Formulation (Direct Compression)

| Ingredients | mg/tablet | mg/tablet | mg/tablet |
|---|---|---|---|
| trans-3-(6-Isopropyl-4-oxo-4H-quinazolin-3-yl)-2-propenoic acid | 1 | 5 | 25 |
| Lactose | 221 | 217 | 197 |
| Avicel | 45 | 45 | 45 |
| Direct Compression Starch | 30 | 30 | 30 |
| Magnesium Stearate | 3 | 3 | 3 |
| Weight of Tablet | 300 mg. | 300 mg. | 300 mg. |

Procedure:
1. Mix trans-3-(6-isopropyl-4-oxo-4H-quinazolin-3-yl)-2-propenoic acid with equal amount of lactose. Mix well.
2. Mix with Avicel and direct compression starch, and remaining amount of lactose. Mix well.
3. Add magnesium stearate and mix for 3 minutes.
4. Compress on a suitable punch.

EXAMPLE 53

Tablet Formulation (Wet Granulation)

| Ingredients | mg/tablet | mg/tablet | mg/tablet |
|---|---|---|---|
| trans-3-(6-Isopropyl-4-oxo-4H-quinazolin-3-yl)-2-propenoic acid | 1 | 5 | 25 |
| Lactose | 202 | 198 | 223 |
| Modified Starch | 25 | 25 | 30 |
| Pregelatinized Starch | 20 | 20 | 20 |
| Distilled water q.s. | — | — | — |
| Magnesium Stearate | 2 | 2 | 2 |

-continued

| Ingredients | mg/tablet | mg/tablet | mg/tablet |
|---|---|---|---|
| Weight of Tablet | 250 mg. | 250 mg. | 300 mg. |

Procedure:
1. Mix trans-3-(6-isopropyl-4-oxo-4H-quinazolin-3-yl)-2-propenoic acid in a suitable mixer.
2. Granulate with sufficient distilled water to proper consistency. Mill.
3. Dry in a suitable oven.
4. Mill and mix with magnesium stearate.
5. Compress on a suitable press equipped with appropriate punches.

EXAMPLE 54

Capsule Formulation

| Ingredients | mg/capsule | mg/capsule | mg/capsule |
|---|---|---|---|
| trans-3-(6-Isopropyl-4-oxo-4H-quinazolin-3-yl)-2-propenoic acid | 1 | 5 | 25 |
| Lactose | 253 | 249 | 229 |
| Starch | 30 | 30 | 30 |
| Talc | 15 | 15 | 15 |
| Magnesium Stearate | 1 | 1 | 1 |
| Capsule fill weight | 300 mg. | 300 mg. | 300 mg. |

Procedure:
1. Mix trans-3-(6-isopropyl-4-oxo-4H-quinazolin-3-yl)-2-propenoic acid, lactose and starch in a suitable mixer.
2. Add talc and magnesium stearate and mix for a short period of time.
3. Encapsulate on an appropriate encapsulation machine.

EXAMPLE 55

Tablet Formulation (Wet Granulation)

| Ingredients | mg/tablet | mg/tablet | mg/tablet |
|---|---|---|---|
| trans-3-[6-(Methylthio)-4-oxo-4H-quinazolin-3-yl]-2-propenoic acid | 1 | 5 | 25 |
| Lactose | 202 | 198 | 223 |
| Modified Starch | 25 | 25 | 30 |
| Pregelatinized Starch | 20 | 20 | 20 |
| Distilled water q.s. | — | — | — |
| Magnesium Stearate | 2 | 2 | 2 |
| Weight of tablet | 250 mg. | 250 mg. | 300 mg. |

Procedure:
1. Mix trans-3-[6-(methylthio)-4-oxo-4H-quinazolin-3-yl]-2-propenoic acid, lactose, modified starch and pregelatinized starch in a suitable mixer.
2. Granulate with sufficient distilled water to proper consistency. Mill.
3. Dry in a suitable oven.
4. Mill and mix with magnesium stearate.
5. Compress on a suitable press equipped with appropriate punches.

EXAMPLE 56

Capsule Formulation

| Ingredients | mg/capsule | mg/capsule | mg/capsule |
|---|---|---|---|
| trans-3-[6-(Methylthio)-4-oxo-4H-quinazolin-3-yl]-2-propenoic acid | 1 | 5 | 25 |
| Lactose | 253 | 249 | 229 |
| Starch | 30 | 30 | 30 |
| Talc | 15 | 15 | 15 |
| Magnesium Stearate | 1 | 1 | 1 |
| Capsule fill weight | 300 mg. | 300 mg. | 300 mg. |

Procedure:
1. Mix trans-3-[6-(methylthio)-4-oxo-4H-quinazolin-3-yl]-2-propenoic acid, lactose and starch in a suitable mixer.
2. Add talc and magnesium stearate and mix for a short period of time.
3. Encapsulate on an appropriate encapsulation machine.

EXAMPLE 57

Tablet Formulation (Direct Compression)

| Ingredients | mg/tablet | mg/tablet | mg/tablet |
|---|---|---|---|
| trans-3-[6-(methylthio)-4-oxo-4H-quinazolin-3-yl]-2-propenoic acid | 1 | 5 | 25 |
| Lactose | 221 | 217 | 197 |
| Avicel | 45 | 45 | 45 |
| Direct Compression Starch | 30 | 30 | 30 |
| Magnesium Stearate | 3 | 3 | 3 |
| Weight of tablet | 300 mg. | 300 mg. | 300 mg. |

Procedure:
1. Mix trans-3-[6-(methylthio)-4-oxo-4H-quinazolin-3-yl]-2-propenoic acid with equal amounts of lactose. Mix well.
2. Mix with avicel, direct compression starch, and remaining amount of lactose. Mix well.
3. Add magnesium stearate and mix for 3 minutes.
4. Compress on a suitable punch.

We claim:
1. A compound of the formula

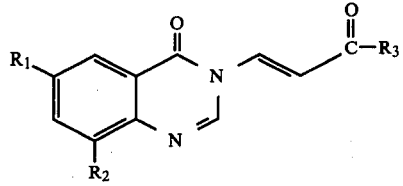

wherein $R_1$ is lower alkyl, lower cyclo-$(C_3-C_7)$-alkyl, lower alkoxy, hydroxy, halo, lower alkylthio, lower alkylsulfinyl, lower alkylsulfonyl, di-$(C_1-C_7)$alkyl N$(CH_2)_n$O— or 2-hydroxyethoxy; $R^2$ is hydrogen; and $R_3$ is hydroxy, lower alkoxy, di-$(C_1-C_7)$alkyl N$(CH_2)_n$O— or di-$(C_1-C_7)$alkyl N$(CH_2)_n$NH—; and wherein n is 2 to 7, when $R_3$ is hydroxy, a salt thereof with a pharmaceuticallly acceptable base, or when $R_3$ is di-$(C_1-C_7)$alkyl-N$(CH_2)_n$O— or di-$(C_1-C_7)$alkyl-N$(CH_2)_n$NH—, a salt thereof with a pharmaceutically acceptable acid.

2. A compound in accordance with claim 1, wherein $R_3$ is hydroxy.

3. A compound in accordance with claim 1, wherein $R_3$ is di-$(C_1-C_7)$alkyl-N$(CH_2)_n$NH.

4. A compound in accordance with claim 3, wherein $R_1$ is lower alkyl.

5. A compound in accordance with claim 2, wherein $R_1$ is lower alkylthio.

6. A compound in accordance with claim 2, wherein $R_1$ is lower alkoxy.

7. A compound in accordance with claim 1, trans 3-(6-isopropyl-4-oxo-4H-quinazolin-3-yl)-2-propenoic acid.

8. A compound in accordance with claim 1, trans-3-[6-(methylthio)-4-oxo-4H-quinazolin-3-yl]-2-propenoic acid.

9. A compound in accordance with claim 1, trans 3-[6-isopropyl-4-oxo-4H-quinazolin-3-yl]-2-propenoic acid, 2-(diethylamino)ethyl amide hydrochloride.

10. A compound in accordance with claim 1, trans-3-(6-isopropoxy-4-oxo-4H-quinazolin-3-yl)-2-propenoic acid.

11. A compound in accordance with claim 1, trans-3-(6-hydroxy-4-oxo-4H-quinazolin-3-yl)-2-propenoic acid.

12. A compound in accordance with claim 1, trans-3-[6-(methylsulfinyl)-4-oxo-4H-quinazolin-3-yl]-2-propenoic acid.

* * * * *